United States Patent [19]

Kobayashi

[11] Patent Number: 4,688,565

[45] Date of Patent: Aug. 25, 1987

[54] ARTIFICIAL RESPIRATOR AUTOMATICALLY RELEASING RESPIRATION PATH SIMULTANEOUS WITH OCCURRENCE OF UNIT FAILURE OF POWER INTERRUPTION

[75] Inventor: Makoto Kobayashi, Kyoto, Japan

[73] Assignee: Sharp Kabushiki Kaisha, Osaka, Japan

[21] Appl. No.: 912,143

[22] Filed: Sep. 24, 1986

Related U.S. Application Data

[63] Continuation of Ser. No. 694,839, Jan. 25, 1985, abandoned.

[30] Foreign Application Priority Data

Jan. 26, 1984 [JP] Japan ............................. 59-9963[U]

[51] Int. Cl.$^4$ ........................................... A61M 16/00
[52] U.S. Cl. ........................... 128/204.19; 128/204.21; 128/205.24
[58] Field of Search ...................... 128/202.22, 202.24, 128/202.27, 203.2, 203.14, 204.18, 204.21, 205.23, 205.24; 251/65

[56] References Cited

U.S. PATENT DOCUMENTS

| | | | |
|---|---|---|---|
| 2,972,465 | 2/1961 | Ray | 251/65 |
| 3,106,205 | 10/1963 | Caldwell | 128/202.22 |
| 3,916,888 | 11/1975 | Buck et al. | 128/204.21 |
| 4,380,233 | 4/1983 | Caillot | 128/203.14 |

*Primary Examiner*—Henry J. Recla
*Attorney, Agent, or Firm*—Birch, Stewart, Kolasch & Birch

[57] ABSTRACT

An extremely useful respirator including a generator circuit for generating signals when the unit either becomes faulty or the power service is suddenly interrupted. The present device is also for opening the respiration circuit in response to the signals thus generated. The respirator reflecting the preferred embodiment eliminates blockage of the respiration circuit when the respirator is faulty or the power service is interrupted during use, thus improving the safety of the patients by applying a simplified mechanism.

4 Claims, 2 Drawing Figures

ARTIFICIAL RESPIRATOR AUTOMATICALLY RELEASING RESPIRATION PATH SIMULTANEOUS WITH OCCURRENCE OF UNIT FAILURE OF POWER INTERRUPTION

This application is continuation of application Ser. No. 694,839 filed on Jan. 25, 1985, and now abandoned.

BACKGROUND OF THE INVENTION

The present invention relates to an artificial respirator. Such an artificial respirator is one of a type of medical treatment equipment allowing a flow of vapor through the respiration circuit in response to a patient's respirations. Since this unit is directly connected to the human body, extreme care should always be execercised to ensure its safe operation. As a safety measure, it is extremely important to ensure prevention of even the slightest interference in respiration under any circumstance during use. More specifically, if for any reason the respiration circuit allows its vapor level to rise beyond a critical level, the respiration circuit should be instantly released in order to decrease the vapor pressure level. Conventional respiration devices made provide a relief valve for ensuring its safe operation. However, when applying a relief valve alone, the respiration valve must be operated at the same time by operating another drive means, and as a result, the safety mechanism is unavoidably complex.

OBJECT AND SUMMARY OF THE INVENTION

In light of the disadvantages still existing in the conventional respiration equipment, the present invention aims at providing a useful artificial respirator incorporating a simplified safety mechanism for effectively preventing blockage of the respiration circuit that otherwise easily occurs when either a mechanical failure or power interruption takes place.

The preferred embodiment of the present invention provides a highly reliable respirator including a generator circuit for generating an emergency signal when either a mechanical failure or power interruption takes place and a device for releasing the respiration circuit in response to the emergency signal thus generated.

DETAILED DESCRIPTION OF THE PREFERRED EMBODIMENT

Figure 1:
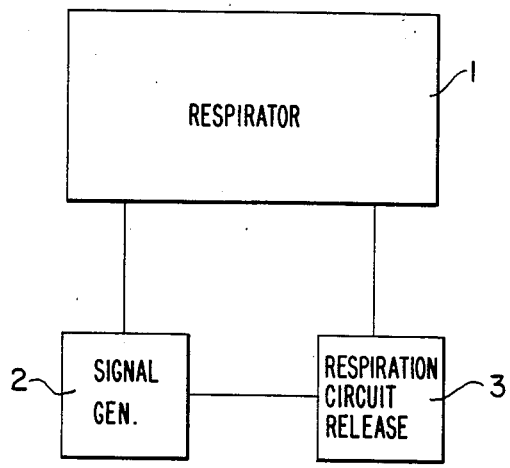
FIG. 1 is a simplified block diagram of the respirator incorporating the preferred embodiment of the present invention.
Figure 2:
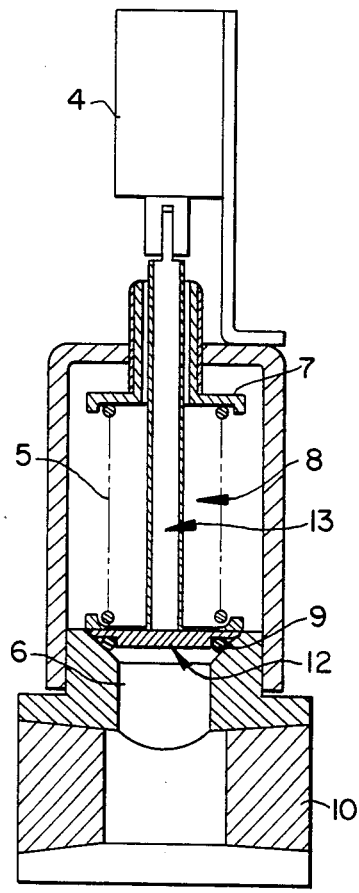
FIG. 2 is a sectional view of the respirator reflecting the preferred embodiment shown in FIG. 1.

Operation and structure of the preferred embodiment of the respirator related to the present invention are described below. FIG. 1 is a simplified block diagram of the respirator reflecting the preferred embodiment of the present invention. In FIG. 1, reference number 1 indicates the respirator unit, to which the signal generator circuit 2 and the respiration circuit releaser 3 are respectively connected. The signal generator circuit 2 generates an emergency signal when either the respirator 1 becomes faulty or the power service being supplied to the respirator 1 is suddenly interrupted. The emergency signal being generated is directly transmitted to the respiration circuit releaser 3. Upon receipt of the emergency signal, the respiration circuit releaser 3 instantly releases the respiration circuit of the respirator 1 to avoid allowing vapor levels to become critical. Referring now to FIG. 2, details of the respiration circuit releaser 3 are described below.

In FIG. 2, reference numbers 4 through 10 and 12-14 indicate the following:

No. 4: Keep solenoid
No. 5: Spring
No. 6: Release outlet
No. 7: Spring holder
No. 8: Valve
No. 9: O-ring
No. 10: Respiration circuit
No. 12: Valve Head
No. 13: Valve Stem
No. 14: Permanent Magnet As shown in FIG. 2, an iron core of keep solenoid 4 is coupled to the valve stem 13 of valve 8, thus jointly enabling vertical movement of the iron core, and valve 8. The valve head 12 (the tip portion of the valve which is not coupled to the keep solenoid 4) of the valve 8 is shaped into a flat plate having a specific size enough to shield the opening of a release outlet 6 provided on the lateral surface of the respiration circuit 10. The head 12 of the valve 8 opens and closes the release outlet 6 in accordance with the vertical movement performed by a coupled unit including the iron core of the keep solenoid 4 and the valve 8. An O-ring 9 is wound onto the head of the valve 8 to ensure complete shielding of the release outlet. Accordingly, when the valve head 12 is in a closed position, release of vapor pressure through the release outlet 6 is prevented. On the other hand, when the valve head 12 is in an open position, release of vapor pressure is permitted. Spring 5 is wound onto a column portion of the valve 8 with the bottom of the spring resting on the head 12 of the valve, and the top of the spring abutting the underside of spring holder 7. Using its elastic force, this spring 5 presses the head 12 of the valve 8 downwards, i.e., against the release outlet 6 from the stationary spring holder 7. Normally, the iron core of the keep solenoid 4 is positioned at a location apart from a permanent magnet 14 and is affected by a positive pulse voltage which is fed to the solenoid 4 when activating (starting) the unit power source. In other words, current passing through the solenoid 4 keeps the iron core 11 away from the permanent magent located within the solenoid, thereby maintaining the valve 8 in a position which closes release outlet 6 of the respiration circuit 10. The iron core of the keep solenoid 4 is, therefore, held downward together with the valve 8 due to the elastic force of spring 5 and activation of the solenoid 4. During this stage, the release outlet 6 is securely closed by the valve 8 and the O-ring 9. By shifting the set position of the stationary spring holder 7, physical pressure of the spring 5 against the valve 8 can be adjusted to a specific level as required. Consequently, when the internal pressure of the respiration circuit 10 rises beyond a critical limit (above the force of the spring 5 and solenoid 4), the head 12 of the valve and, thus, the valve 8 are pushed upwards to compress the spring 5 and cause the release outlet 6 to open itself. In this case, the valve head 12 of valve 8 functions as the relief valve itself.

As described earlier, when an emergency signal is generated by the signal generator circuit 2, simultaneously with the occurrence of either the functional failure of the respirator or power interruption, no is fed to the keep solenoid 4. As a result, the iron core of the solenoid 4 is pulled upward by the magnetism of the permanent magnet 14 to render the release outlet 6 in an open position. As is clear from the above detailed description, the respirator incorporating the preferred embodiment of the present invention securely eliminates the slightest blocking of the respiration circuit even if the respirator either becomes faulty or the power service is suddenly interrupted during its use. The present respirator, therefore, improves the safety of the patients by using a simplified mechanism.

What is claimed is:

1. An artificial respirator comprising:
   a respiration circuit with a pressure release outlet therein;
   a valve having a valve housing mounted over said outlet, a valve head reciprocally mounted in said valve housing to close said outlet, and a valve stem having a first end connected to said valve head, said valve head being movable between an open position wherein vapor pressure will be released from said release outlet and a closed position for preventing release of vapor pressure through said release outlet;
   solenoid means with a movable iron core operatively connected to a second end of said valve stem;
   spring means mounted in said housing and operatively connected to said valve head to bias said valve head to said closed position;
   said solenoid means, when activated, in conjunction with said spring means each generating a sufficient force to normally hold said valve head in the closed position until the vapor pressure in the respiration circuit reaches a predetermined limit whereupon the valve head will move to the open position, and after release of vapor pressure from the release outlet, the force of the solenoid means and the force of the spring means will return the valve head to the closed position;
   permanent magnet means located with respect to said iron core for generating a magnetic force that can move said iron core in a direction opposite to that of said spring, said magnetic force being stronger than the force of said spring means;
   means for generating an emergency output signal during emergency operation, said signal deactivating said solenoid means thereby eliminating the force of said solenoid means whereafter said magnetic force is sufficient to overcome the force of the spring means to cause said valve head to move to the open position for release of said vapor pressure from said respiration circuit.

2. An artificial respirator according to claim 1, wherein said emergency operation occurs when there is either a mechanical failure of said respirator or a power interruption to said respirator.

3. An artificial respirator according to claim 1, wherein said spring means is a coil spring which surrounds said valve stem.

4. An artificial respirator according to claim 1, wherein a support for said spring is provided at a location spaced from said valve head, said support being selectively movable to positions longitudinally along said valve stem, whereby adjusting of said support to said positions varies the force of said spring means operatively connected to said valve head.

* * * * *